(12) United States Patent
Al-Amri

(10) Patent No.: US 10,725,014 B2
(45) Date of Patent: Jul. 28, 2020

(54) SALT ANALYZER FOR CRUDE OIL

(71) Applicant: Saudi Arabian Oil Company, Dhahran (SA)

(72) Inventor: Fahad A. Al-Amri, Udhailiyah (SA)

(73) Assignee: Saudi Arabian Oil Company, Dhahran (SA)

( * ) Notice: Subject to any disclaimer, the term of this patent is extended or adjusted under 35 U.S.C. 154(b) by 617 days.

(21) Appl. No.: 15/061,545

(22) Filed: Mar. 4, 2016

(65) Prior Publication Data

US 2017/0254793 A1    Sep. 7, 2017

(51) Int. Cl.
*G01N 33/28* (2006.01)
*C10G 31/08* (2006.01)

(52) U.S. Cl.
CPC .......... *G01N 33/2835* (2013.01); *C10G 31/08* (2013.01); *G01N 33/2823* (2013.01)

(58) Field of Classification Search
CPC .................................................. G01N 33/2835
USPC ........................................................ 73/53.05
See application file for complete search history.

(56) References Cited

U.S. PATENT DOCUMENTS

| | | | |
|---|---|---|---|
| 7,334,450 B1 * | 2/2008 | Scott .................. | G01N 33/2847 702/104 |
| 7,587,290 B2 | 9/2009 | Scott | |
| 7,904,251 B2 | 3/2011 | Martin et al. | |
| 2006/0142955 A1 | 6/2006 | Jones et al. | |
| 2011/0100877 A1 | 5/2011 | Snawerdt | |
| 2013/0026082 A1 * | 1/2013 | Al-Shafei ............. | B01D 17/06 210/96.1 |
| 2014/0131254 A1 | 5/2014 | Soliman | |
| 2017/0018601 A1 | 1/2017 | Park et al. | |

OTHER PUBLICATIONS

The International Search Report and Written Opinion for related PCT application PCT/US17/20564 (SA5473/PCT) dated Jun. 30, 2017; 15 pages.
Bahadori, A.; "Prediction of Formation Water Properties Using a Novel Predictive Tool Approach and Vandermonde Matrix" NAFTA 63 (9-10) 2012; pp. 289-298.
Bahadori, Alireza, et al.; "Estimation of crude oil salt content using a simple predictive tool approach" Journal of Petroleum Science and Engineering 96-97 (2012); pp. 68-72; Note—Retracted Version.

(Continued)

*Primary Examiner* — Nimeshkumar D Patel
*Assistant Examiner* — Jean F Morello
(74) *Attorney, Agent, or Firm* — Bracewell LLP; Constance G. Rhebergen; Brian H. Tompkins

(57) ABSTRACT

Embodiments of the disclosure include a salt analyzer for crude oil. The crude oil salt analyzer includes a salt concentration model that determines a salt concentration from desalting process parameters that may include a demulsifier flowrate, a crude oil temperature, a crude oil flowrate, a desalting electrostatic grids voltage, a wash water flowrate, and a disposal water flow rate. The crude oil salt analyzer may compare the salt concentration to a threshold concentration to determine if the salt concentration exceeds the threshold concentration and may perform or initiate actions based on the comparison. Methods, computer-readable media, and plant information systems using the crude oil salt analyzer are also provided.

12 Claims, 5 Drawing Sheets

(56) References Cited

OTHER PUBLICATIONS

Gobbo, R., et al.; "Modeling, Simulation, and Optimization of a Front-End System for Acetylene Hydrogenation Reactors" Brazilian Journal of Chemical Engineering, vol. 21, No. 04, Oct.-Dec. 2004; pp. 545-556.

Bahadori, Alireza; "Prediction of Salinity of Salty Crude Oil Using Arrhenius-Type Asymptotic Exponential Function and Vandermonde Matrix" SPE 132324, Society of Petroleum Engineers, Mar. 2011 SPE Projects, Facilities & Construction; pp. 27-32.

Doyle, Adriana, et al.; "Direct chlorine determination in crude oils by energy dispersive X-ray fluorescence spectrometry: An improved method based on a proper strategy for sample homogenization and calibration with inorganic standards" Spectrochimica Acta Part B 66 (2011); pp. 368-372.

Fortuny, Montserrat, et al.; "Measuring Salinity in crude oils: Evaluation of methods and improved procedure" ScienceDirect, Fuel 87 (2008); pp. 1241-1248.

Aslan, N.; "Modeling and optimization of Multi-Gravity Separator to produce celestite concentrate" ScienceDirect, Powder Technology 174 (2007); pp. 127-133.

Zhao, B., et al.; "Simulation of Gas Flow Pattern and Separation Efficiency in Cyclone with Conventional Single and Spiral Double Inlet Configuration" Institution of Chemical Engineers, Trans IChemE, Part A, Dec. 2006, Chemical Engineering Research and Design, 84 (A12); pp. 1158-1165.

Li, Kang, et al.; "Modelling and prediction of NOx emission in a coal-fired power generation plant" ScienceDirect Control Engineering Practice 12 (2004); pp. 707-723.

Sayda, Atalla F. and Taylor, James H.; "Modeling and Control of Three-Phase Gravity Separators in Oil Production Facilities" Proceedings of the 2007 American Control Conference New York City, USA, Jul. 11-13, 2007; pp. 4847-4853.

\* cited by examiner

SALT ANALYZER FOR CRUDE OIL

BACKGROUND

Field of the Disclosure

Embodiments of the disclosure generally relate to the production of crude oil and, more particularly, to the determining the concentration of salt in crude oil.

Description of the Related Art

The production of crude oil may involve a number of processes engineered to produce crude oil to specific quality specifications. For example, such quality specifications may specific a maximum amount of salt permitted in crude oil. Thus, the production of crude oil may include processes and techniques to remove salt from crude oil. In some instances, the amount of salt in produced crude oil may be manually monitored by sampling crude oil from the shipped crude pipeline and at time intervals. The sampled crude oil may be titrated with a reference alkaline solution to measure crude salinity. The results of the sampling may provide the amount of salt in crude oil after the crude oil has been produced. However, such sampling may only be used to reactively change process parameters to improve crude oil quality. Moreover, such manual sampling may be tedious and time-consuming and only detects deterioration in crude oil quality after it has occurred in the time interval between samplings.

SUMMARY

Embodiments of the disclosure generally relate to a salt analyzer for crude oil. The crude oil salt analyzer includes a salt concentration model that determines a salt concentration from desalting process parameters. The salt concentration model may be a first order continuous variables model and may be determined using a regression analysis and sample data obtained from a desalting process, such as from an oil-gas separation plant. The crude oil salt analyzer may compare the salt concentration to a threshold concentration to determine if the salt concentration exceeds the threshold concentration and may perform or initiate actions based on the comparison.

In some embodiments, a method for determining a salt concentration in crude oil is provided. The method includes obtaining one or more parameters associated with a desalting process. The desalting process parameters may include a demulsifier flowrate, a crude oil temperature, a crude oil flowrate, a desalting electrostatic grids voltage, a wash water flowrate, and a disposal water flowrate. The method also includes determining the salt concentration in crude oil output from the desalting process using the one or more desalting process parameters. In some embodiments, the method further includes comparing the determined salt concentration to a threshold concentration and providing a notification if the salt concentration exceeds the threshold concentration. In some embodiments, the notification includes activation of an alarm in a plant information system. In some embodiments, providing a notification includes providing a notification to a plant information client in communication with a plant information system. In some embodiments, the method also includes obtaining a sample of crude oil output from the desalting process and comparing the determining the salt concentration to a salt concentration determined from the crude oil sample. In some embodiments, determining the salt concentration in crude oil output from the desalting process includes determining the salt concentration using a first order continuous variables model. In some embodiments, determining the salt concentration in crude oil output from the desalting process includes determining the salt concentration according to the following:

$$\text{Salt PTB} = \beta_0 + \beta_1 A + \beta_2 B + \beta_3 C + \beta_4 D + \beta_5 E + \beta_6 F + \varepsilon$$

such that Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D is the desalting electrostatic grids voltage, E is the wash water flowrate in gallons per minute (GPM), F is the disposal water rate in MBD, $\varepsilon$ is a random error term, and $\beta_0$, $\beta_1$, $\beta_2$, $\beta_3$, $\beta_4$, $\beta_5$, and $\beta_6$ are factor effects. In some embodiments, the method further includes adjusting at least one of the one or more parameters associated with a desalting process if the salt concentration exceeds the threshold concentration.

In some embodiments, a non-transitory computer-readable storage medium having executable code stored thereon for determining a salt concentration in crude oil is provided. The executable code includes a set of instructions that causes a plant information processor to perform operations that include obtaining one or more parameters associated with a desalting process. The desalting process parameters may include a demulsifier flowrate, a crude oil temperature, a crude oil flowrate, a desalting electrostatic grids voltage, and a wash water flowrate. The operations also include determining the salt concentration in crude oil output from the desalting process using the one or more desalting process parameters. In some embodiments, the operations further include comparing the determined salt concentration to a threshold concentration and providing a notification if the salt concentration exceeds the threshold concentration. In some embodiments, the notification includes activation of an alarm in a plant information system. In some embodiments, providing a notification if the salt concentration exceeds the threshold concentration includes transmitting, over a network, a notification to a plant information client of a plant information system. In some embodiments, determining the salt concentration in crude oil output from the desalting process includes determining the salt concentration using a first order continuous variables model. In some embodiments, determining the salt concentration in crude oil output from the desalting process includes determining the salt concentration according to the following:

$$\text{Salt PTB} = \beta_0 + \beta_1 A + \beta_2 B + \beta_3 C + \beta_4 D + \beta_5 E + \beta_6 F + \varepsilon$$

such that Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D is the desalting electrostatic grids voltage, E is the wash water flowrate in GPM, F is the disposal water rate in MBD, and $\varepsilon$ is a random error term, and $\beta_0$, $\beta_1$, $\beta_2$, $\beta_3$, $\beta_4$, $\beta_5$, and $\beta_6 F$ are factor effects. In some embodiments, the operations further include adjusting at least one of the one or more parameters associated with a desalting process if the salt concentration exceeds the threshold concentration.

In some embodiments, a plant information system is provided that includes a plant information processor and a non-transitory computer-readable storage memory accessible by the plant information processor and having executable code stored thereon for determining the a salt concentration in crude oil. The executable code includes a set of instructions that causes a plant information processor to perform operations that include obtaining one or more parameters associated with a desalting process. The desalting process parameters may include a demulsifier flowrate, a crude oil temperature, a crude oil flowrate, a desalting electrostatic grids voltage, and a wash water flowrate. The operations also include determining the salt concentration in crude oil output from the desalting process using the one or more desalting process parameters. In some embodiments, the operations further include comparing the determined salt concentration to a threshold concentration and providing a notification if the salt concentration exceeds the threshold concentration. In some embodiments, the notification includes activation of an alarm in the plant information system. In some embodiments, the plant information system includes a plant information client such that providing a notification if the salt concentration exceeds the threshold concentration includes transmitting, over a network, a notification to the plant information client. In some embodiments, plant information client includes a display, such that the plant information client provides a visual notification on the display in response to receipt of the notification. In some embodiments, obtaining one or more parameters associated with a desalting process includes receiving the one or more parameters over an industrial control network coupled to the plant information system. In some embodiments, determining the salt concentration in crude oil output from the desalting process includes determining the salt concentration using a first order continuous variables model. In some embodiments, determining the salt concentration in crude oil output from the desalting process includes determining the salt concentration according to the following:

$$\text{Salt PTB} = \beta_0 + \beta_1 A + \beta_2 B + \beta_3 C + \beta_4 D + \beta_5 E + \beta_6 F + \varepsilon$$

such that Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D is the desalting electrostatic grids voltage, E is the wash water flowrate in GPM, F is the disposal water rate in MBD, and $\varepsilon$ is a random error term, and $\beta_0$, $\beta_1$, $\beta_2$, $\beta_3$, $\beta_4$, $\beta_5$, and $\beta_6 F$ are factor effects.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

Figure 1:
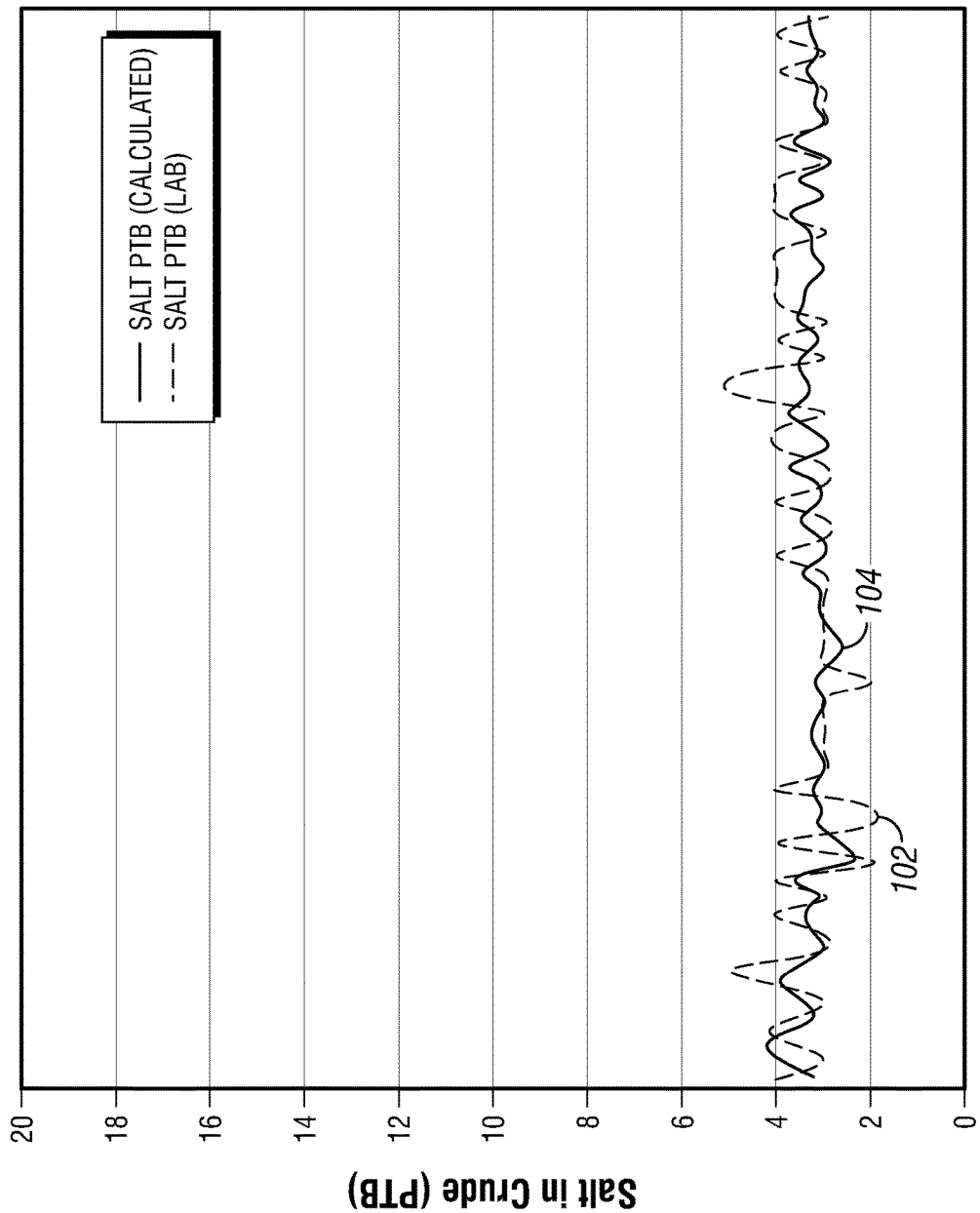
FIG. 1 is a chart comparing the actual salt concentration determined by laboratory analysis and the salt concentration calculated by the salt concentration model in accordance with embodiments of the disclosure.

The present disclosure will now be described more fully hereinafter with reference to the accompanying drawings, which illustrate embodiments of the disclosure. This disclosure may, however, be embodied in many different forms and should not be construed as limited to the illustrated embodiments set forth herein. Rather, these embodiments are provided so that this disclosure will be thorough and complete, and will fully convey the scope of the disclosure to those skilled in the art.

Embodiments of the disclosure include a salt analyzer for crude oil that receives desalting process parameters and determines the amount of salt in the desalted crude oil. The crude oil salt analyzer includes a salt concentration model that determines the salt concentration in crude oil from the desalting process parameters. In some embodiments, the desalting process parameters include a demulsifier flowrate, a crude oil temperature, a crude oil flowrate, a desalting electrostatic grids voltage, a wash water flowrate, and a disposal water flowrate. The crude oil salt analyzer may determine the salt concentration without interruption of the desalting process, without physically sampling the crude oil, and may provide faster determinations of salt concentration as compared to laboratory analysis of crude oil samples. Additionally, the crude oil salt analyzer may provide for predictions of salt concentration and maintenance of a desired salt concentration in the crude oil.

In some embodiments, the virtual salt analyze may compare the determined salt concentration to a threshold concentration. If the determined salt concentration is below the threshold concentration, the crude oil salt analyzer may continue monitoring of the desalting process parameters and the salt concentration. If the determined salt concentration is above the threshold concentration, a notification, such as a notification in a plant information (PI) system, may be provided. In some embodiments, if the determined salt concentration is above the threshold concentration, the desalting process parameters may be adjusted, such as via a distributed control system (DCS).

In some embodiments, the crude oil salt analyzer may be implemented in a plant information system in communication with a desalting process. In such embodiments, the plant information system may receive desalting process parameters from the desalting process and the crude oil salt analyzer may determine the salt concentration in crude oil output from the desalting process using the salt concentration model. In such embodiments, in response to a determined salt concentration, the plant information system may provide the salt concentration, a notification, or both to in communication with the plant information system. In some embodiments, the plant information client may include a display that displays an alert in response to the notification or other data received from the plant information system.

The salt analyzer for crude oil includes a salt concentration model that determines the salt concentration from different desalting parameters. The salt concentration model is a first order continuous variables model generated from correlations between desalting process parameters and the crude oil salt concentration. In some embodiments, the first order continuous variables model used in the crude oil salt analyzer may be represented by Equation 1:

$$\text{Salt PTB} = \beta_0 + \beta_1 A + \beta_2 B + \beta_3 C + \beta_4 D + \beta_5 E + \beta_6 F + \varepsilon \quad (1)$$

Where:
Salt PTB is the salt concentration in pounds of salt per thousand barrels of crude oil;
$\beta_0$, $\beta_1$, $\beta_2$, $\beta_3$, $\beta_4$, and $\beta_5$ are factor effects;
A is the demulsifier flowrate in gallons per day (GPD);
B is the crude oil temperature in degrees Fahrenheit;

C is the crude oil rate in one thousand barrels per day (MBD);

D is the voltage of the desalting grids (for example, the electrostatic grids used in the desalter);

E is the wash water flowrate in GPM;

F is the disposal water rate in MBD; and

ε is a random error term.

Examples

The following examples are included to demonstrate embodiments of the disclosure. It should be appreciated by those of skill in the art that the techniques and compositions disclosed in the example which follows represents techniques and compositions discovered by the inventors to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

A salt concentration model was generated from an experiment using a central composite design that provided a total of thirty runs according to the desalting parameter constraints discussed below. In the experiment, the demulsifier rate was generated at a normal rate (in GPD), the normal rate+X (in GPD) and the normal rate−X (in GPD). The crude oil temperature was measured at the maximum, average, and minimum points, that is at 14:00, 20:00, and 02:00 respectively. The oil rate was not controlled. The desalting electrical grid voltages were in the range of 19 kilovolts (kV) to 24 kV. The wash water flowrate was generated at a normal rate (in GPM), the normal rate+X (in GPM) and the normal rate−X (in GPM). The disposal water rate was not controlled.

The data was sampled between noon, afternoon, and nighttime to ensure all parameter constraints and the experiment design was met. For example, the demulsifier rate may be about 140 GPD at nighttime, about 90 GPD at noon, and about 115 GPD in the afternoon.

The null hypothesis for the experiment was that all five parameters (the demulsifier flowrate, crude oil temperature, oil rate, desalting grids voltage, and water rate) do not significantly affect the crude oil salt concentration. According to this null hypothesis, β0, β1, β2, β3, β4, and β5 in Equation 1 were assumed to equal zero, such that all parameters in Equation 1 do not affect crude oil salt concentration. The confidence interval was identified at 95% (that is, α=0.05), such that there is a 5% change of committing a type I error (that is, erroneously rejecting the null hypothesis when it is actually true). The hypothesis was evaluated based on the p-value obtained by regression analysis using the MegaStat® tool for Microsoft Excel® provided by McGraw-Hill Education of New York City, N.Y., USA. If the p-value associated with a parameter is less than 0.05, then the null hypothesis is rejected and the parameter is considered to be significant with regard to the crude oil salt concentration. If the p-value associated with a parameter is greater than 0.05, then the null hypothesis is not rejected and the parameters is considered to be not significant with regard to the crude oil salt concentration.

Using the model and experiment design described supra, an example experiment was conducted at a gas-oil separation plant (GOSP) and data was collected per the ordered runs. For example, Tables 1 and 2 show sampled data collection runs for the first three days of the experiment

TABLE 1

Sampled Data Collection Runs for Three Days

| Order # | Day | Demulsifier Rate (GPD) | Time of Sample | Wash water flowrate (GPM) | Oil Rate (MBD) |
| --- | --- | --- | --- | --- | --- |
| 1 | 1st Day | Normal − 10 GPD | 14:00 | Normal − 10 GPM | To be recorded as per the process, as this parameter was not controlled during sampling |
| 2 | 1st Day | Normal + 10 GPD | 20:00 | Normal | |
| 3 | 2nd Day | Normal | 2:00 | Normal +10 GPM | |
| 4 | 2nd Day | Normal + 10 GPD | 14:00 | Normal + 10 GPM | |
| 5 | 2nd Day | Normal − 10 GPD | 20:00 | Normal − 10 GPM | |
| 6 | 3rd Day | Normal + 10 GPD | 2:00 | Normal | |
| 7 | 3rd Day | Normal + 10 GPD | 14:00 | Normal − 10 GPM | |
| 8 | 3rd Day | Normal − 10 GPD | 20:00 | Normal − 10 GPM | |
| 9 | 4th Day | Normal | 2:00 | Normal − 10 GPM | |

TABLE 2

Sampled Data Collection Runs for Three Days

| Order # | Day | Disposal Water Rate (MBD) | Crude Oil Temperature (° F.) | Desalting Grids Voltage | Salt Concentration (PTB) |
| --- | --- | --- | --- | --- | --- |
| 1 | 1st Day | To be recorded as per the process, as this parameter was not controlled during sampling. | To be recorded as per the process. This parameter was controlled by taking the samples at the highest, middle and lowest crude oil temperature (at 14:00 hrs, 20:00 hrs and 02:00 hrs respectively). The crude oil temperature was determined by the ambient weather since there was no inlet heating process. | To be recorded as per the process, as this parameter was not controlled during sampling. | Obtained by laboratory analysis for each sample |
| 2 | 1st Day | | | | |
| 3 | 2nd Day | | | | |
| 4 | 2nd Day | | | | |
| 5 | 2nd Day | | | | |
| 6 | 3rd Day | | | | |
| 7 | 3rd Day | | | | |
| 8 | 3rd Day | | | | |
| 9 | 4th Day | | | | |

After thirty runs, the collected data was modeled using the MegaStat® tool in Excel® to conduct regression analysis using Equation 1. Using this analysis, the factor effects β0, β1, β2, β3, β4, and β5 in Equation 1 were obtained to produce a salt concentration model for the example oil-gas separation plant. The salt concentration model was then verified by comparing the actual salt concentration determined by laboratory analysis with the salt concentration calculated by the salt concentration model. FIG. 1 is a chart 100 comparing the actual salt concentration determined by laboratory analysis and the salt concentration calculated by the salt concentration model. The vertical axis in FIG. 1 depicts the salt concentration in desalted crude oil in PTB. As shown in FIG. 1, the line 102 depicts the salt concentration determined using the salt concentration model of the virtual salt and line 104 depicts the salt concentration determined by laboratory analysis.

For the data obtained in the runs at the example oil-gas separation plant, the salt concentration model may be based on Equation 1 and represented by Equation 2:

$$\text{Salt PTB} = 4.935 - 0.0145*A + 0.005351*F + 0.0265*C - 0.0343*B \quad (2)$$

According to the example indicated in Equation 2, $\beta 1$ is −0.0145, $\beta 6$ is 0.005351, $\beta 3$ is 0.0265, $\beta 2$ is −0.0343, and $\varepsilon$ is 4.935.

Generation of Salt Concentration Model

Figure 2:
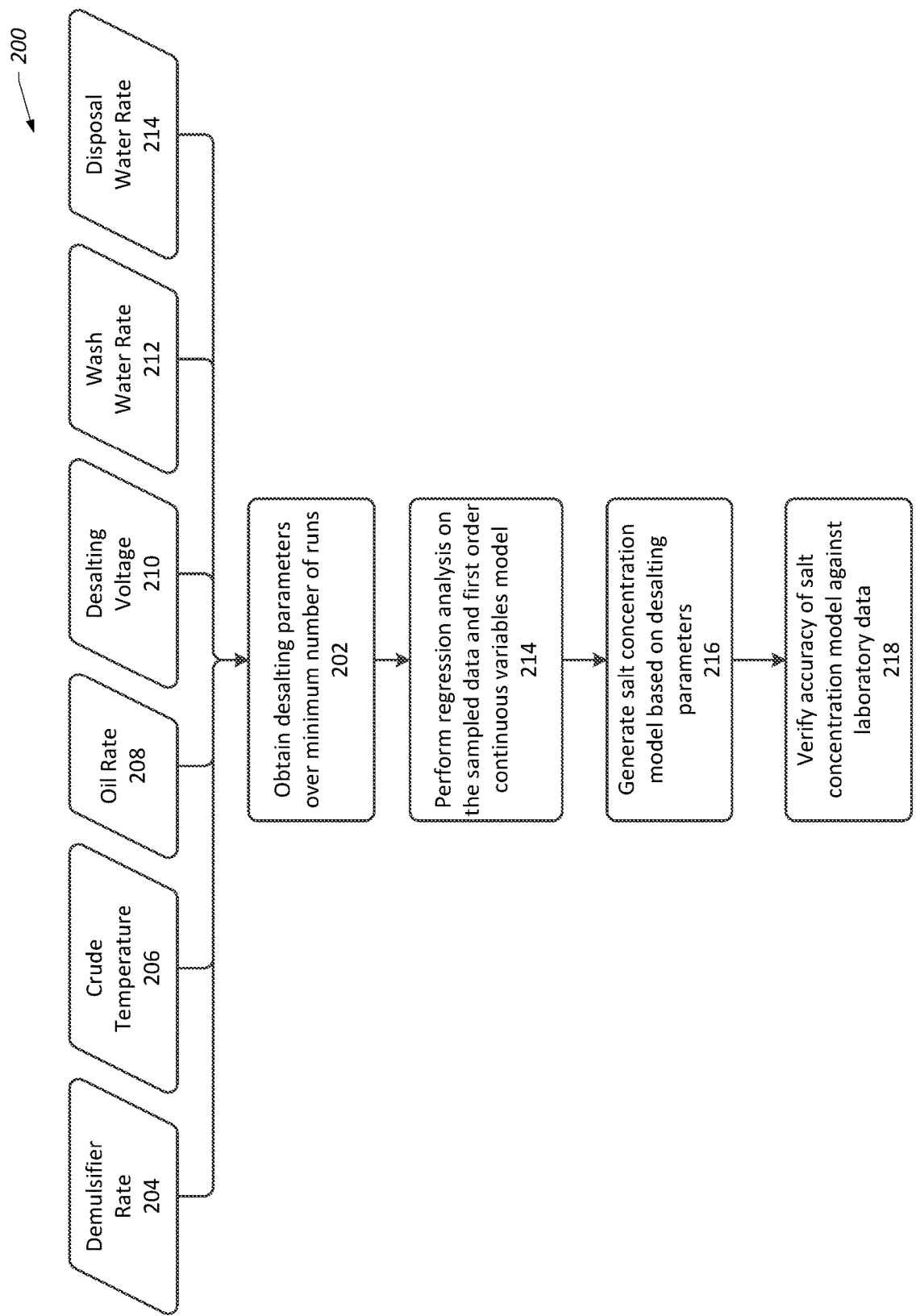
FIG. 2 is a block diagram of a process for generation of a salt concentration model for a salt analyzer for crude oil in accordance with embodiments of the disclosure.

In light of the above discussion, FIG. 2 depicts a process 200 for generation of a salt concentration model for a salt analyzer for crude oil in accordance with embodiments of the disclosure. Initially, desalting process parameters may be sampled over a minimum number of runs (202). For example, desalting process parameters may be sampled from a desalting process of a gas-oil separation plant. In some embodiment, the desalting process parameters may be sampled at different times of day over multiple days to meet the minimum number of runs. In some embodiments, a desalting process parameter may be varied over the sampling, such that the desalting process parameter may be sampled at a normal value, a normal value+X, and a normal value−X.

In some embodiments, the desalting process parameters may include demulsifier rate 204 (measured in GPD), crude temperature 206 (measured in ° F.), oil rate 208 (measured in MBD), desalting electrical grids voltage 210 (measured in kV), wash water flowrate 212 (measured in GPM), and disposal water rate (measured in GPM). In some embodiments, for example, sampling of the desalting process parameters may include sampling the demulsifier rate at a normal rate, a normal rate+X, and a normal rate−X. In some embodiments, other desalting process parameters may be varied in a similar manner.

Using the null hypothesis and Equation 1 described above, a regression analysis may be performed on the sampled data and the first order continuous variables model described in Equation 1 (block 214) using, for example, a suitable statistical analysis tool. The regression analysis may determine the factor effects for each desalting process parameter. A salt concentration model for a desalting process may then be generated from the regression analysis (block 216) for use in the crude oil salt analyzer. In some embodiments, the accuracy of the salt concentration model may be verified by comparing the calculated salt concentration from the model against actual salt concentrations from laboratory analysis (block 218). For example, in some embodiments a sample may include the desalting process parameters for use in the generated salt concentration model and a sample of desalted crude oil for use in laboratory analysis. The generated salt concentration model may be used to determine a salt concentration from the sampled desalting process parameters, and the actual salt concentration may be determined via laboratory analysis of the desalted crude oil sample. In some embodiments, multiple salt concentrations determined using the salt concentration model and actual salt concentration from laboratory analysis may be obtained over a time period to provide verification of the salt concentration model.

Example Implementations of Crude Oil Salt Analyzer

Figure 3:
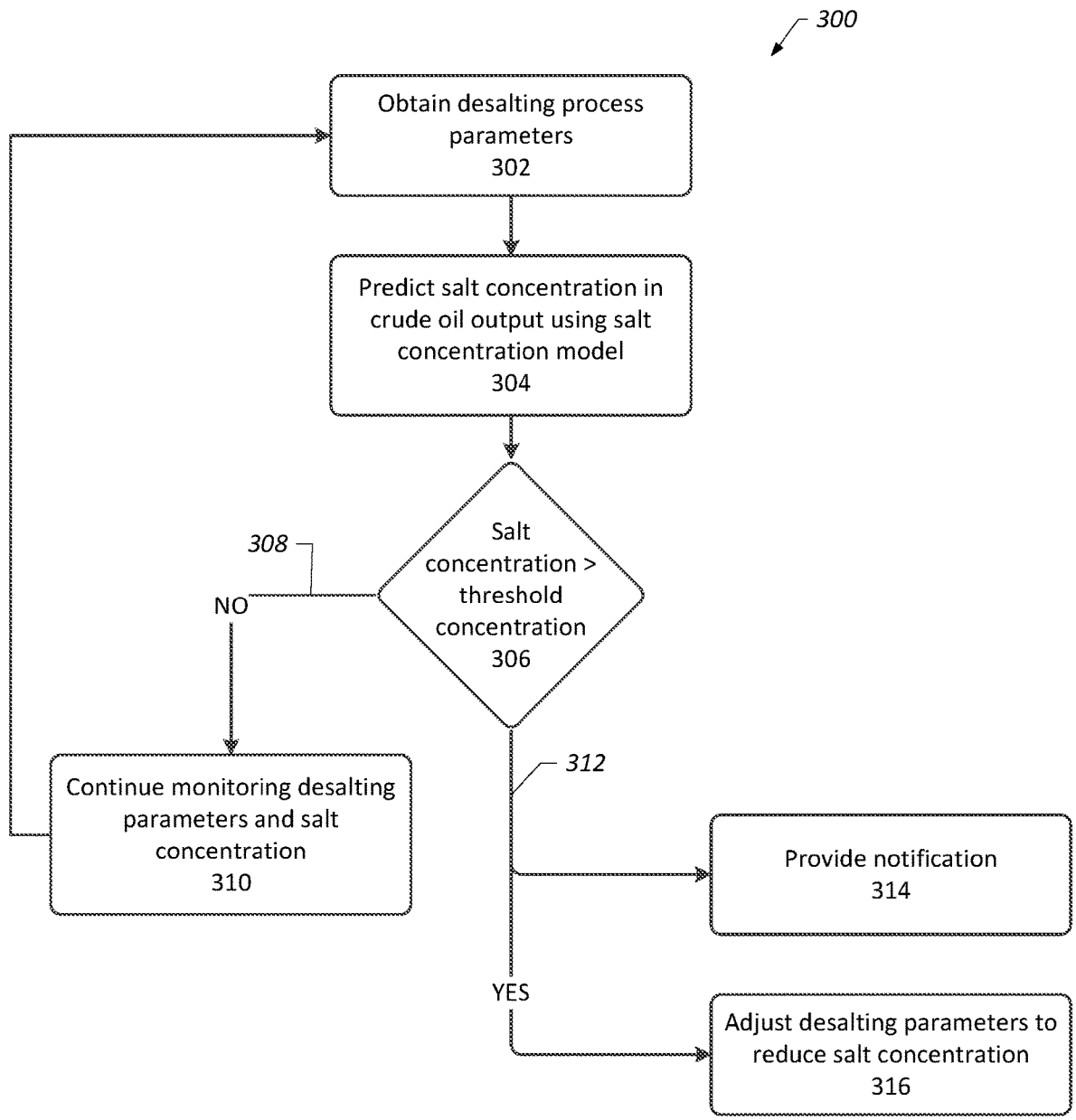
FIG. 3 is a block diagram of a process for using a crude oil salt analyzer having a salt concentration model in accordance with embodiments of the disclosure.

FIG. 3 depicts a process 300 for using a crude oil salt analyzer having a salt concentration model in accordance with embodiments of the disclosure. In some embodiments, the process 300 may be implemented using a plant information system, a distributed control system, or a combination of these systems. For example, in some embodiments a virtual salt analyze and the corresponding process 300 may be implemented in a plant information system of an oil and gas separation plant.

In some embodiments, the process 300 may be performed periodically, that is at regular periods or at irregular periods. For example, in some embodiments the process 300 may be performed three times a day between equal time intervals, such that desalting process parameters are obtained and a salt concentration is determined between equal time intervals. In some embodiments, the process 300 may be performed once a day, twice a day, or more than three times a day. In some embodiments, the process 300 may be performed continuously, such that changes in desalting process parameters are continuously obtained and used to determine a salt concentration in desalted crude oil. Additionally or alternatively, in some embodiments the process 300 may be performed on-demand, that is when requested, such as by an operator at a gas-oil separation plant. In other embodiments, desalting process parameters may be obtained at a different period than the determination of salt concentration. For example, desalting process parameters may be obtained at a relatively frequent rate (e.g., between relatively short periods) such that relatively recent parameters are readily available whenever a salt concentration determination is requested.

Initially, desalting parameters may be obtained from a desalting process (block 302). For example, desalting parameters may be obtained from sensors or other suitable components configured to monitor parameters of a desalting process. In some embodiments, for example, the sensors may be a part of or send data to a plant information (PI) system or a distributed control system (DCS) over a suitable communications network.

Next, the salt concentration in the crude oil output may be determined using the salt concentration model of the crude oil salt analyzer (block 304). As described above, for example, a salt concentration model for the desalting process and based on Equation 1 may be generated using the process 200 described above and illustrated in FIG. 2. The generated salt concentration model may then be used to determine a salt concentration for the desalting process.

In some embodiments, the determined salt concentration may be compared to a threshold concentration to determine whether the determined salt concentration has exceeded the threshold concentration (decision block 306). For example, the crude oil output from the desalting process may have a maximum allowable salt concentration. The threshold concentration may thus be based on a maximum allowable salt concentration for the crude oil output or may be another salt concentration. In some embodiments, for example, the maximum allowable salt concentration in the desalted crude oil may 10 PTB.

In some embodiments, the crude oil salt analyzer and the salt concentration model may be used to determine a baseline salt concentration over a time period or a number of samples. In some embodiments, the threshold concentration may be equal or based on such as baseline salt concentration established using the crude oil salt analyzer and the salt concentration model. In some embodiments, crude oil salt analyzer and the salt concentration model may be used to predict a baseline salt concentration based on changes in the desalting process parameters.

If the salt concentration has not exceeded the threshold concentration (line 308), then desalting parameters and salt concentration may continue to be monitored (block 310). For example, the desalting parameters may again be obtained (block 302), such as after a time interval, and the salt concentration may be determined using the salt concentration model 304). As mentioned above, the monitoring of the desalting parameters and salt concentration may be performed periodically to establish regular monitoring of a desalting process.

In some embodiments, if the determined salt concentration has exceeded the threshold concentration (line 312), a notification may be provided (block 314). For example, the notification may include a communication such as an email message or text message, an alert, activation of an alarm, other suitable notifications or combination thereof. The notification may include a visual notification, (for example, a visual alert or alarm) may be provided on a display device, an audio notification (for example, an audio alert or alarm) provided on an audio output device, or both. In some embodiments providing a notification may include the activation of an alarm in a plant information system. Thus, in some embodiments, the techniques described in the disclosure may be used to determine an alarm associated with crude oil salt concentration. In some embodiments, the crude oil salt analyzer and the salt concentration model may be used to determine a baseline salt concentration, a threshold concentration and notifications based on deviations from a threshold concentration.

In some embodiments, if the determined salt concentration has exceeded the threshold concentration (line 312), one or more of the desalting parameters may be adjusted to reduce the salt concentration in the crude oil output (block 316). In some embodiments each obtained desalting process parameter may be compared to a baseline value and, depending on the comparison, may be increased or decreased to return to the baseline value. In some embodiments, the factor effects of the salt concentration model may be used as an indicator of the effect on salt concentration of the deviation of a desalting process parameter from the baseline. Thus, in some embodiments the crude oil salt analyzer may perform or initiate an action in response to the determination of a salt concentration.

In some embodiments, the crude oil salt analyzer may proactively predict changes in salt concentration and provide a determined salt concentration, notification, or both to enable changes in the desalting process parameters before the actual salt concentration in the desalted crude oil exceeds a threshold concentration.

Figure 4:
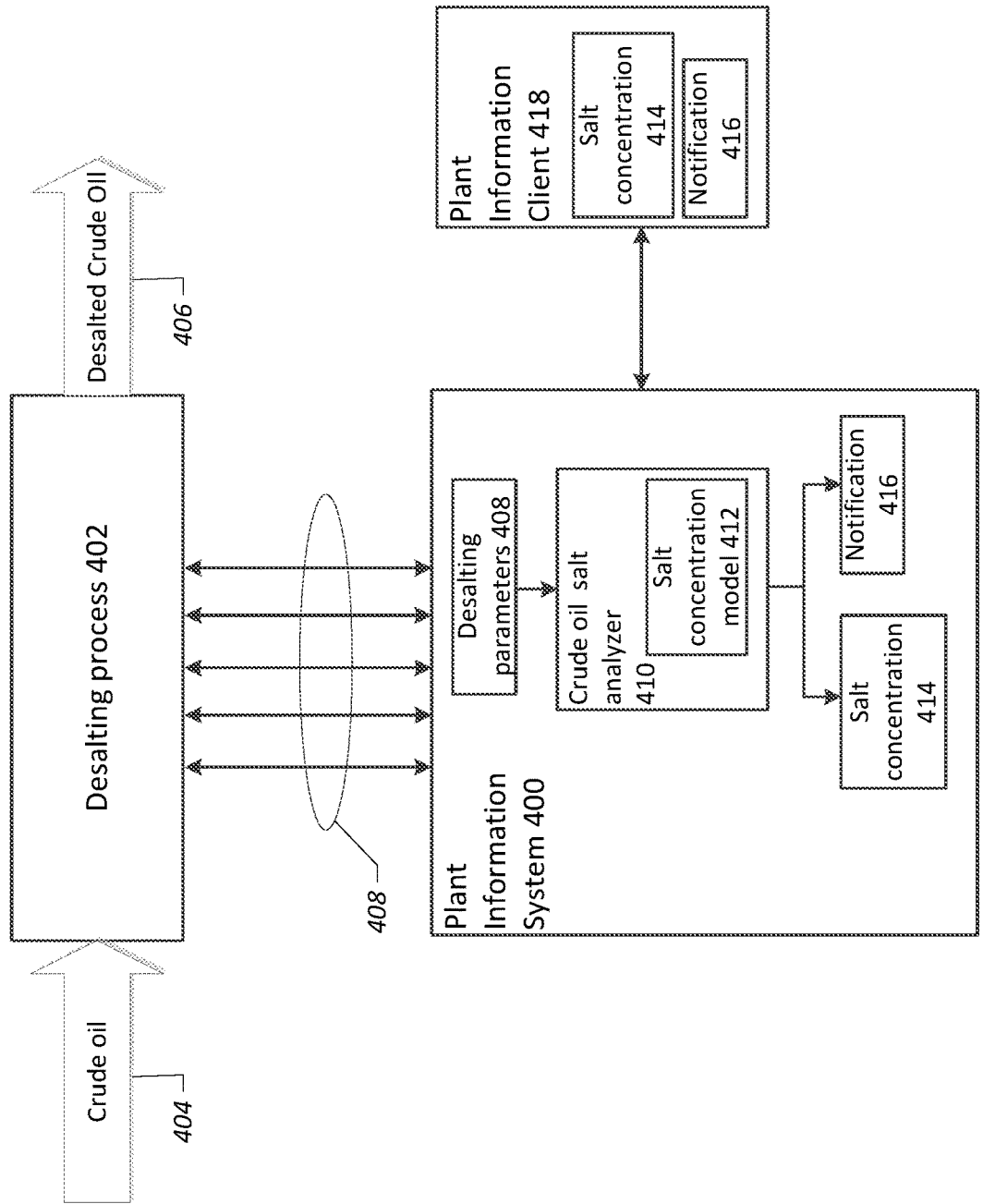
FIG. 4 is a schematic diagram of a plant information system in communication with a desalting process 402 in accordance with embodiments of the disclosure.

In some embodiments, a crude oil salt analyzer having a salt concentration model may be implemented in a plant information system. FIG. 4 depicts a plant information system 400 in communication with a desalting process 402 in accordance with an embodiment of the disclosure. In some embodiments, the plant information system 400 may interface with a distributed control system (not shown) that controls various components that control and monitor the desalting process 402. It should be appreciated that, in other embodiments, a crude oil salt analyzer having salt concentration model may be implemented in the distributed control system instead of the plant information system.

The desalting process 402 may receive crude oil 404 having a relatively high salt content and output desalted crude oil 406. The desalting process 402 may include any suitable desalting processes and techniques, such as single stage desalters and multi-stage desalters that use electrostatic desalting. As shown in FIG. 4, the plant information system 400 may receive desalting process parameters 408 from the desalting process 402. For example, the desalting process parameters may be measured using suitable components arranged at various locations around the desalting process. Such components may include sensors such as flowmeters, temperature sensors (e.g., thermometers or thermocouples), voltage sensors, and so on. Such components may be a part of the plant information system 400 or a distributed control system, or may be communication with the plant information system 400 or distributed control system via a suitable communication network.

As described above, the desalting parameters 408 may be provided to a crude oil salt analyzer 410. The crude oil salt analyzer 410 may implement a salt concentration model 412 determined in accordance with the techniques described in the disclosure. The crude oil salt analyzer 410 may receive the desalting parameters 408 and determine a salt concentration 414 for the desalted crude oil 406 output from the desalting process 402. As described above, in some embodiments the crude oil salt analyzer 410 may obtain the desalting parameters 408 and determine the salt concentration 414 periodically or upon request, such as from an operator interfacing with the plant information system 400. In some embodiments, as described above, the crude oil salt analyzer may provide a notification 416 if the salt concentration exceeds a threshold concentration. For example, in some embodiments the notification may include the activation of an alarm of the plant information system 400.

In some embodiments, a plant information client 418 may be in communication with the plant information system 400. For example, the plant information client may provide plant information to an operator and enable monitoring of various process parameters. In such embodiments, the plant information system 400 may provide information to the plant information client 418 about the desalting process 402. For example, the plant information system 400 may provide the salt concentration 414 determined by the crude oil salt analyzer 410 to the plant information client 418. Alternatively or additionally, in some embodiments the plant information system 400 may provide the notification 416 to the plant information client 418. For example, in some embodiments the notification 416 may include an alarm displayed on the plant information client that indicates that the salt concentration 414 has exceeded a threshold concentration. The notification 416 may, for example, enable an operator to take actions regarding any changes in salt concentration provided via the plant information client 418.

Figure 5:
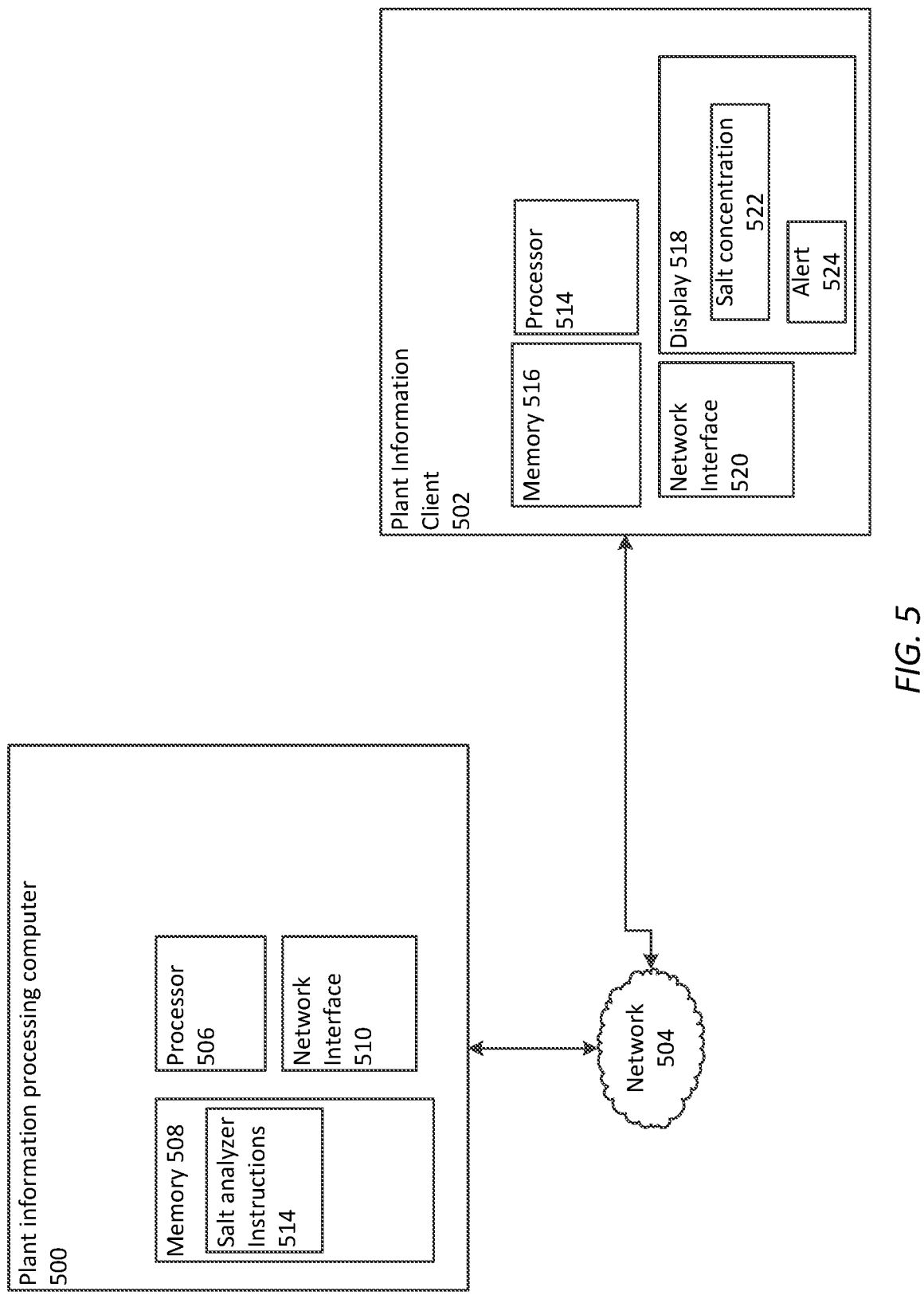
FIG. 5 is a schematic diagram of components of a plant information processing computer and a plant information client in accordance with an embodiment of the disclosure.

FIG. 5 depicts components of a plant information processing computer 500 and a plant information client 502 in accordance with an embodiment of the disclosure. The plant information processing computer 500 may be a part of a plant information system, such as the plant information system 400 described above, and may be communication with the plant information client 502 via a network 504. In some embodiments, the plant information computer 500 may be in communication with other components of a plant information system, such as other plant information processing computers and components that receive data from processes, a distributed control system, or both. It should be appreciated that an example plant information system may include multiple plant information processing computers and, in some embodiments, various actions described herein may be implemented on multiple plant information processing computers or distributed to different plant information processing computers (for example, in some instances a plant information process computer may obtain desalting process parameters for a desalting process and a second plant information process computer may execute a crude oil salt analyzer that receives the desalting process parameters and determines a salt concentration in crude oil output from the desalting process.

As shown in FIG. 5, the plant information processing computer 500 may include a plant information processor 506, a memory 508, and a network interface 510. It should be appreciated that the plant information processing computer may include other components that are omitted for clarity.

The plant information processor 506 (as used the disclosure, the term "processor" encompasses microprocessors) and may include one or more processors having the capability to receive and process plant information, such as data received from sensors, a distributed control system, and other plant components and systems. In some embodiments, the plant information processor 506 may include an application-specific integrated circuit (AISC). In some embodiments, the plant information processor 506 may include a reduced instruction set (RISC) processor. Additionally, the plant information processor 506 may include a single-core processors and multicore processors and may include graphics processors. Multiple processors may be employed to provide for parallel or sequential execution of one or more of the techniques described in the disclosure. The plant information processor 506 may receive instructions and data from a memory (for example, memory 508).

The memory 508 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 508 may be accessible by the plant information processor 506. The memory 508 may store executable computer code. The executable computer code may include computer program instructions for implementing one or more techniques described in the disclosure, For example, the executable computer code may include the crude oil salt analyzer instructions 514 executable by a processor (for example, the processor 506) to implement one or more embodiments of the present disclosure. In some embodiments, the crude oil salt analyzer instructions 514 may implement one or more elements of process 300 described supra and illustrated in FIG. 3. For example, in some embodiments, the crude oil salt analyzer instructions 514 may define a crude oil salt analyzer that may receive desalting process parameters and determine a crude oil salt concentration from the desalting process parameters. The crude oil salt concentration may be stored in the memory 508.

The network interface 510 may provide for communication between the plant information computer 500 and other devices, such as other plant information computers and the plant information client 502. The network interface 510 may include a wired network interface card (NIC), a wireless (e.g., radio frequency) network interface card, or combination thereof. The network interface 510 may include circuitry for receiving and sending signals to and from communications networks, such as an antenna system, an RF transceiver, an amplifier, a tuner, an oscillator, a digital signal processor, and so forth. The network interface 510 may communicate with networks (e.g., network 504), such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (e.g., IEEE 802.11 standards), and other standards, protocols, and technologies. In some embodiments, the network interface 510 may enable communication over industrial control networks.

As mentioned above, the plant information processing computer 500 may be in communication with the plant information client 502 via the network 504. As shown in FIG. 5, the plant information client may include a plant information client processor 514, a memory 516, a display 518 and a network interface 520. It should be appreciated that the plant information client 502 may include other components that are omitted for clarity.

The plant information client processor 514 (as used the disclosure, the term "processor" encompasses microprocessors) and may include one or more processors having the capability to receive and process information received from the plant information processing computer 500. In some embodiments, the plant information processor 514 may include an application-specific integrated circuit (AISC) or a reduced instruction set (RISC) processor. The plant information processor 514 may also include a single-core processors and multicore processors and may include graphics processors. The plant information processor 514 may receive instructions and data from the memory 516.

The memory 516 (which may include one or more tangible non-transitory computer readable storage mediums) may be accessible by the plant information client processor 514 and include volatile memory, such as random access memory (RAM), and non-volatile memory, such as ROM, flash memory, a hard drive, any other suitable optical, magnetic, or solid-state storage medium, or a combination thereof. The memory 508 may store executable computer code that may include, for example, executable computer code for displaying information received from the plant information processing computer 500.

The display 518 may include a cathode ray tube (CRT) display, liquid crystal display (LCD), an organic light emitting diode (OLED) display, or other suitable display. The display 518 may display a user interface (for example, a graphical user interface) that may display information received from the plant information processing computer 500. In accordance with some embodiments, the display 518 may be a touch screen and may include or be provided with touch sensitive elements through which a user may interact with the user interface. In some embodiments, the display 518 may display a crude oil salt concentration 522 received from the plant information processing computer 500 and determined by a crude oil salt analyzer in accordance with the techniques described herein. In some embodiments, the display 518 may display a notification, such as alert 524, received from the plant information processing computer or determined from information (e.g., the salt concentration 522) provided by the plant information processing computer. For example, in some embodiments the plant information processing computer 500 may transmit a notification to the plant information client 502 via the network 504. In some embodiments, the plant information processing computer 500 may transmit additional or other data that subsequently activates the alert 524 on the plant information client 502.

The network interface 520 may provide for communication between the plant information client 502 and the plant information processing computer 500 and, in some embodiments, between the plant information client 502 and other devices. The network interface 520 of the plant information client 502 may, in some embodiments, be similar to the network interface 510 of the plant information processing computer 500. Accordingly, in some embodiments the network interface 510 include a wired network interface card (NIC), a wireless (e.g., radio frequency) network interface card, or combination thereof. The network interface 520 may include circuitry for receiving and sending signals to and from communications networks, such as an antenna system, an RF transceiver, an amplifier, a tuner, an oscillator, a digital signal processor, and so forth. The network interface 520 may communicate with networks (e.g., network 504), such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (e.g., IEEE 802.11 standards), and other standards, protocols, and technologies. In some embodiments, the network interface 520 may enable communication over industrial control networks.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described herein. It is to be understood that the forms shown and described herein are to be taken as examples of embodiments. Elements and materials may be substituted for those illustrated and described herein, parts and processes may be reversed or omitted, and certain features may be utilized independently, all as would be apparent to one skilled in the art after having the benefit of this description. Changes may be made in the elements described herein without departing from the spirit and scope of the disclosure as described in the following claims. Headings used herein are for organizational purposes only and are not meant to be used to limit the scope of the description.

What is claimed is:

1. A method for determining a salt concentration in crude oil, comprising:
    periodically obtaining at a time interval, at a plant information system, a plurality of parameters associated with a desalting process, the plurality of desalting process parameters comprising a demulsifier flowrate, a crude oil temperature, a crude oil flowrate, a desalting electrostatic grids voltage, a wash water flowrate, and a disposal water flowrate;
    determining, at the plant information system, the salt concentration in crude oil output from the desalting process using the plurality of parameters according to a first order continuous variables model;
    comparing the determined salt concentration to a threshold concentration; and
    adjusting at least one of the plurality of parameters associated with the desalting process based on the comparison.

2. The method of claim 1, comprising providing a notification to a plant information client in communication with the plant information system based on the comparison.

3. The method of claim 1, comprising:
    obtaining a sample of crude oil output from the desalting process; and
    comparing the determined salt concentration to a salt concentration determined from the crude oil sample.

4. The method of claim 1, wherein determining the salt concentration in crude oil output from the desalting process using the plurality of desalting process parameters comprises determining the salt concentration according to the following:

Salt PTB=β0+β1$A$+β2$B$+β3$C$+β4$D$+β5$E$+β6$F$+ε wherein Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D is the desalting electrostatic grids voltage, E is the wash water flowrate in gallons per minute (GPM), F is the disposal water flowrate in MBD, ε is a random error term, and β0, β1, β2, β3, β4, β5, and β6 are factor effects.

5. A non-transitory computer-readable storage medium having executable code stored thereon for determining the a salt concentration in crude oil, the executable code comprising a set of instructions that causes a plant information processor to perform operations comprising:
    periodically obtaining at a time interval, at a plant information system, a plurality of parameters associated with a desalting process, the desalting process parameters comprising a demulsifier flowrate, a crude oil temperature, a crude oil flowrate, a desalting electrostatic grids voltage, a wash water flowrate, and a disposal water flowrate; and
    determining, at the plant information system, the salt concentration in crude oil output from the desalting process using the plurality of parameters according to a first order continuous variables model;
    comparing the determined salt concentration to a threshold concentration; and
    adjusting at least one of the plurality of parameters associated with the desalting process based on the comparison.

6. The non-transitory computer-readable storage medium of claim 5, the operations comprising providing a notification to a plant information client in communication with the plant information system based on the comparison.

7. The non-transitory computer-readable storage medium of claim 5, wherein determining the salt concentration in crude oil output from the desalting process using the one or more desalting process parameters comprises determine the according to the following:

Salt PTB=β0+β1$A$+β2$B$+β3$C$+β4$D$+β5$E$+β6$F$+ε wherein Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D desalting electrostatic grids voltage, E is the wash water flowrate in gallons per minute, F is the disposal water flowrate in MDB, ε is a random error term, and β0, —(31, —(32, β3, β4, β5, and β6 are factor effects.

8. A plant information system, comprising:
    a plant information processor;
    a non-transitory computer-readable storage memory accessible by the plant information processor and having executable code stored thereon for determining the salt concentration in crude oil, the executable code comprising a set of instructions that causes the plant information processor to perform operations comprising:
        periodically obtaining at a time interval, at the plant information processor, a plurality of parameters associated with a desalting process, the plurality of desalting process parameters comprising a demulsifier flowrate, a crude oil temperature, a crude oil flowrate, a desalting electrostatic grids voltage, a wash water flowrate, and a disposal water flowrate; and determining, at the plant information processor, the salt concentration in crude oil output from the desalting process using the plurality of desalting process parameters according to a first order continuous variables model;

comparing the determined salt concentration to a threshold concentration; and adjusting at least one of the plurality of parameters associated with the desalting process based on the comparison.

9. The plant information system of claim 8, comprising a plant information client, the operations comprising providing a notification to the plant information client based on the comparison.

10. The plant information system of claim 9, wherein the plant information client comprises a display, wherein the plant information client provides a visual notification on the display in response to receipt of the notification.

11. The plant information system of claim 8, wherein determining the salt concentration in crude oil output from the desalting process using the one or more desalting process parameters comprises determine the according to the following:

$$\text{Salt PTB} = \beta 0 + \beta 1 A + \beta 2 B + \beta 3 C + \beta 4 D + \beta 5 E + \beta 6 F + \varepsilon$$

wherein Salt PTB is the salt concentration in pounds of salt per thousand barrels of crude oil, A is the demulsifier flowrate in gallons per day (GPD), B is the crude oil temperature in degrees Fahrenheit, C is the crude oil rate in one thousand barrels per day (MBD), D is the desalting electrostatic grids voltage, E is the wash water flowrate in gallons per minute (GPM), F is the disposal water rate in MBD, $\varepsilon$ is a random error term, and $\beta 0$, $\beta 1$, $\beta 2$, $\beta 3$, $\beta 4$, $\beta 5$, and $\beta 6$ are factor effects.

12. The plant information system of claim 8, wherein periodically obtaining between a time interval, at the plant information processor, a plurality of parameters associated with a desalting process comprises receiving the plurality of desalting process parameters over an industrial control network coupled to the plant information system.

\* \* \* \* \*